United States Patent [19]
Goldstein et al.

[11] Patent Number: 5,461,020
[45] Date of Patent: Oct. 24, 1995

[54] DIALKYL AMINO PYRIDINE CATALYSTS WHICH ARE BOUND TO INORGANIC MATRICES AND PROCESSES FOR THEIR PREPARATION

[75] Inventors: Stephen L. Goldstein, Cheshire, Conn.;
Anthony D. Hamer, Northbrook, Ill.;
Lawrence E. Katz, Orange, Conn.;
Michael J. McGeary, Meriden, Conn.;
Curtis P. Smith, Cheshire, Conn.

[73] Assignee: Olin Corporation, Cheshire, Conn.

[21] Appl. No.: 241,249

[22] Filed: May 11, 1994

Related U.S. Application Data

[63] Continuation-in-part of Ser. No. 43,075, Apr. 5, 1993, Pat. No. 5,315,004.

[51] Int. Cl.$^6$ .................................................. B01J 31/26
[52] U.S. Cl. ........................................................ 502/167
[58] Field of Search ............................................ 502/167

[56] References Cited

U.S. PATENT DOCUMENTS

| | | | |
|---|---|---|---|
| 4,912,210 | 3/1990 | Disteldorf et al. | 540/202 |
| 5,315,004 | 5/1994 | Goldstein et al. | 540/202 |

*Primary Examiner*—Asok Pal
*Attorney, Agent, or Firm*—Dale L. Carlson

[57] ABSTRACT

This invention relates to a catalyst composition comprising the reaction product of (a) an inorganic substrate containing a reactive hydroxyl group and selected from the group consisting of silica compounds, alumina compounds, and combinations thereof, (b) a catalyst containing terminal unsaturation and selected from the group consisting of 4-dialkylamino pyridines, 4-(N-arylalkyl-N-alkyl)amino pyridines, and combinations thereof, and (c) a hydrosilane. Also disclosed is a process for making the catalyst composition, as well as the catalyst composition by empirical structural formula.

15 Claims, No Drawings

1

DIALKYL AMINO PYRIDINE CATALYSTS WHICH ARE BOUND TO INORGANIC MATRICES AND PROCESSES FOR THEIR PREPARATION

This is a continuation-in-part application of U.S. Ser. No. 08/043,075, filed Apr. 5, 1993, now U.S. Pat. No. 5,315,004.

FIELD OF THE INVENTION

This invention relates generally to aminopyridine catalysts, and, more specifically, to 4-dialkylamino and 4-(N-arylalkyl-N-alkyl)-aminopyridines that are covalently bound to an inorganic matrix substrate.

BACKGROUND OF THE INVENTION

Polyuretidione adducts of polyisocyanates are intermediates which can be used in the preparation of high performance urethane coatings, paints, and films. These adducts provide reduced volatility and an associated reduced toxicity hazard during use, as compared to monomeric polyisocyanates, such as, for example, toluene diisocyanate. In addition, because of their low viscosity, isocyanato uretidiones can be used as reactive diluents for other highly viscous or solid isocyanate group containing coatings components or as a polyisocyanate component in solvent-free and low solvent coatings formulations.

Processes for preparing these adducts are well known. Examples illustrative of these processes can be found in U.S. Pat. Nos. 4,476,054; 4,912,210; and 4,929,724. Generally, the prior art processes involve adding a soluble catalyst which promotes the isocyanate to uretidione (also known as "dimerization") reaction of the precursor isocyanate, optionally in the presence, but usually in the absence, of a solvent, allowing the reaction to proceed to the desired extent and then stopping the reaction with a suitable quenching agent which destroys the activity of the catalyst. Alternatively, in the cases where relatively volatile catalysts are used, the reaction is stopped by distilling the catalyst along with the residual, unreacted precursor isocyanate from the product dimer.

After the residual, unreacted precursor isocyanate is removed, the resulting material, in the case where the precursor isocyanate is a diisocyanate, is a mixture of oligomers composed of 2, 3, 4, etc. precursor diisocyanate molecules joined by 1, 2, 3, etc. uretidione rings. Usually, this mixture is simply called "dimer".

In the case where the precursor isocyanate is polyisocyanate, the reaction is generally stopped well before all the isocyanate groups have been converted to uretidione groups because, otherwise, the resulting product would be an unusable polymer having a very high (theoretically infinite) molecular weight and viscosity. However, the cost of equipment and energy to remove residual, unreacted precursor isocyanate dictate that the reaction not be stopped too soon. Generally, the reaction is run to more than 10% conversion but less than 50% conversion. The preferred range is between 20 and 35%. The reaction is typically stopped using a quenching agent. The reaction between conventional dimerization catalysts and quenching agents typically results in the formation of an insoluble product which is typically removed by filtration using a filter aid.

Unfortunately, both the quenching agent and the filter aid increase the likelihood of introducing undesirable impurities into the product. Accordingly, catalyst compositions for producing dimers, that do not employ nor require a quenching agent and filter aid(s) during use of the catalyst, would be highly desired by the dimer manufacturing community.

One approach to meeting this need employs a catalyst that is covalently bound to an insoluble organic substrate, as disclosed for example in U.S. Pat. No. 5,015,706. The catalysts disclosed in the '706 patent include so-called "DMAP" and "BMAP" catalysts which fall within the generic classes of catalysts called 4-dialkylaminopyridines and 4-(N-arylalkyl-N-alkyl)amino-pyridines. These classes of catalysts are useful in a variety of reactions, including acylation, urethane formation and uretidione formation. These catalysts have the structure $Pyr-NR_1R_2$ (I) where Pyr is a 4-pyridinyl residue and $R_1$ and $R_2$ are, independently from one another, $C_1$ to $C_6$ alkyl or $C_7$ to $C_{12}$ arylalkyl groups, or, $R_1$ and $R_2$, taken together with the attached nitrogen, form a ring which may contain other heteroatoms, such as oxygen, nitrogen or sulfur, to give, for example, pyrrolidine, piperidine or morpholine residues. Common examples of 4-dialkylaminopyridines are 4-dimethylaminopyridine (referred to as "DMAP", structure I where $R_1$ and $R_2$ are $CH_3$) and 4-pyrrolidinylpyridine (structure I where $R_1$ and $R_2$, taken together, are $(CH_2)_4$) while 4-(N-arylalkyl-N-alkyl)aminopyridines are exemplified by 4-(N-benzyl-N-methyl)aminopyridine (referred to as "BMAP", structure I where $R_1$ is $CH_2C_6H_5$ and $R_2$ is $CH_3$). A survey of the use of DMAP catalysts, by E. F. V. Scriven, is published in *Chem. Soc. Rev.*, 129 (1983). Another review of DMAP chemistry, by G. Hofle, W. Steglich and H. Vorbruggen can be found in *Angew. Chem. Int. Ed. Engl.*, 17, 569 (1978).

The advantages associated with the use of 4-dialkylaminopyridine and 4-(N-arylalkyl-N-alkyl)aminopyridine catalyst bound to an insoluble matrix, such as the organic polymer matrix disclosed in the above-mentioned '706 patent and the references cited in that patent, have been long recognized. These advantages include the simplified separation of the catalyst from a reaction mixture, the potential of recovering and reusing the catalyst, as well as the ready adaptability of these catalysts for use in static and flow reaction systems.

Unfortunately, it is now recognized that organic polymer substrates have shortcomings during use. These shortcomings are especially evident when the starting materials have two or more reactive sites in each molecule and the resulting products are oligomeric or polymeric, such as polyurethane polyisocyanates or polyuretidione polyisocyanates. These desired products are typically non-volatile liquids or amorphous solids. It is difficult, if not impossible from a practical standpoint, to remove essentially all process contaminants from these types of products. In the former case, where polyurethane polyisocyanates are formed by the catalyzed reaction of, for example, a diisocyanate with, for example, a diol, the resulting product is a mixture of oligomers composed of 2, 3, 4, etc. precursor diisocyanate molecules joined by 1, 2, 3, etc. alcohol residues through urethane bonds. Usually, these types of product mixtures are simply called "isocyanate terminated prepolymers". In the latter case, involving the preparation of polyuretidione polyisocyanates by the catalyzed dimerization of, for example, (cyclo)aliphatic diisocyanates, after removal of the residual, unreacted precursor diisocyanate, the resulting product is a mixture of oligomers composed of 2, 3, 4, etc. precursor diisocyanate molecules joined by 1, 2, 3, etc. uretidione rings. Usually, this mixture is simply called "dimer".

Before 4-dialkylaminopyridine or 4-(N-arylalkyl-N-alkyl)amino-pyridine catalysts bound to an organic polymer can be used to prepare the above-mentioned products, it is necessary to subject the as-produced resin to a rigorous pretreatment to remove low molecular weight substrate oligomers that would otherwise be extracted from the resin and, thereby, contaminate the desired product. Even with such a pretreatment, moderate, but undesirable, levels of color can be formed during the dimerization reaction and in the urethane formation processes. In addition, another, most significant, problem is attributable to the accumulation of product oligomers within the substrate's resin matrix during the reaction. Such fouling continuously reduces the activity of the catalyst resin and thereby limits its useful lifetime. Further, the trapped oligomers can not be easily washed from the substrate. Instead, these entrapped product oligomers represent an undesirable product yield loss and necessitate the use of very rigorous conditions to regenerate the catalyst resin for reuse. Moreover, in some cases the catalysts cannot be regenerated even under rigorous conditions.

While, in principle, the aforementioned problems can be reduced through the use of more highly cross-linked ("macroporous" or "macroreticular") organic polymers, these problems are not entirely eliminated, since residual migration of the reactant(s) into the resin apparently occurs. Further, it is difficult to prepare such polymers having practical levels of catalytic sites available on the surface of the resin bead.

It should be readily apparent, in view of the above discussion, that new catalyst compositions which avoid the above-described problems of catalyst fouling, product yield loss, and product contamination, would be highly desired by the polyisocyante-based coatings manufacturing community. The present invention provides one solution to this problem.

SUMMARY OF THE INVENTION

In one aspect, the present invention relates to a catalyst composition having the following empirical structural formula: cat-(—Si—(—0-inorg substr)$_m$)$_n$ wherein "cat" denotes an aminopyridine catalyst selected from the group consisting of 4-dialkylamino and 4-(N-arylalkyl-N-alkyl)-aminopyridines, and combinations thereof, wherein "inorg substr" denotes an inorganic substrate selected from the group consisting of silica compounds, alumina compounds, and combinations thereof, wherein m is between one and three, and wherein n is between one and two, said aminopyridine catalyst having the structure Pyr-NR1R2 wherein Pyr is a 4-pyridinyl residue, and $R_1$ and $R_2$ are, independently from one another, $C_1$ to $C_6$ alkyl or $C_7$ to $C_{12}$ arylalkyl groups, or, $R_1$ and $R_2$, taken together with the attached nitrogen, form a ring optionally containing another heteroatom selected from the group consisting of oxygen, nitrogen, sulfur, and combinations thereof.

In another aspect, the present invention relates to a catalyst composition comprising the reaction product of (A) an inorganic substrate containing a reactive hydroxyl group and selected from the group consisting of silica compounds, alumina compounds, and combinations thereof, (B) an aminopyridine catalyst containing terminal unsaturation and selected from the group consisting of 4-dialkylamino and 4-(N-arylalkyl-N-alkyl)-aminopyridines, and combinations thereof, said aminopyridine catalyst having the structure Pyr-NR1R2 wherein Pyr is a 4-pyridinyl residue, and $R_1$ and $R_2$ are, independently from one another, $C_1$ to $C_6$ alkyl or $C_7$ to $C_{12}$ arylalkyl groups, or, $R_1$ and $R_2$, taken together with the attached nitrogen, form a ring optionally containing another heteroatom selected from the group consisting of oxygen, nitrogen, sulfur, and combinations thereof, and (C) a hydrosilane.

In yet another aspect, the present invention relates to a process for preparing a catalyst composition which comprises the steps of:

(a) reacting a terminally unsaturated aminopyridine catalyst selected from the group consisting of 4-dialkylamino and 4-(N-arylalkyl-N-alkyl)-aminopyridines, and combinations thereof, said aminopyridine catalyst having the structure Pyr-NR1R2 wherein Pyr is a 4-pyridinyl residue, and $R_1$ and $R_2$ are, independently from one another, $C_1$ to $C_6$ alkyl or $C_7$ to $C_{12}$ arylalkyl groups, or, $R_1$ and $R_2$, taken together with the attached nitrogen, form a ring optionally containing another heteroatom selected from the group consisting of oxygen, nitrogen, sulfur, and combinations thereof, with a hydrosilane to cause hydrosilanization of the catalyst, thereby providing a hydrosilanized catalyst containing at least one —SiX moiety wherein "X" is halogen or OR wherein "R" is an alkyl group of 1–25 carbons, and (b) reacting said hydrosilanized catalyst with an inorganic substrate containing a reactive hydroxyl group and selected from the group consisting of silica compounds, alumina compounds, and combinations thereof, to provide an inorganic substrate-bound catalyst composition characterized by the presence of at least one siloxy linking moiety providing covalent bonding between said catalyst and said substrate.

These and other aspects will become apparent upon reading the following detailed description of the invention.

DETAILED DESCRIPTION OF THE INVENTION

In accordance with the present invention, it has now been surprisingly discovered that a catalyst composition suitably prepared by causing a catalyst to be covalently bound to an inorganic substrate by means of a siloxy moiety. The catalyst composition is useful not only as a dimerization catalyst in dimerization reactions, but also as a catalyst for esterification, urethanization, and acylation, as well as a catalyst for producing biurets and allophanates. In principle, when using the catalyst compositions of the present invention, all of the above described problems arising from the dissolution of the reactant(s) into the catalytic substrate are circumvented. Heretofore, such catalyst systems have not been known to the knowledge of the present inventors.

The catalysts suitable for use in preparing the catalyst compositions of the present invention are suitably tertiary amines that are advantageously aminopyridines selected from the group consisting of 4-dialkylamino and 4-(N-arylalkyl-N-alkyl)aminopyridines, and combinations thereof. These catalysts are suitably bound to an inorganic matrix in accordance with the process of the present invention. These compositions bear the structure Pyr-NR1R2 (I) where Pyr is a 4-pyridinyl residue, and $R_1$ and $R_2$ are, independently from one another, $C_1$ to $C_6$ alkyl or $C_7$ to $C_{12}$ arylalkyl groups, or, $R_1$ and $R_2$, taken together with the attached nitrogen, form a ring which may contain another heteroatoms, such as oxygen, nitrogen or sulfur, to give, for example, pyrrolidine, piperidine or morpholine residues. The compositions of the present invention are further characterized by the covalent bonds that attach structure I to an inorganic matrix through R1 and/or R2.

In a particularly advantageous aspect of the present invention, 4-dialkylamino and 4-(N-arylalkyl-N-alkyl)amino pyridine catalysts which are covalently bound to an insoluble inorganic matrix are prepared and employed in a straightforward fashion to provide facile acylation, urethane formation and uretidione formation reactions. The term "catalysts which are covalently bound to an insoluble inorganic matrix" as used herein is intended to designate bound catalysts which are insoluble in the reaction medium by virtue of the inorganic support, and thus are easily separated from the reaction medium by removal of the bound catalyst from the reaction medium after the reaction has proceeded to the desired extent of completion.

The inorganic supports that can be employed in the preparation of the catalyst compositions of this invention should be inert and "essentially insoluble" (i.e., not soluble to any substantial degree) in the reaction medium. Additional factors to be considered in selecting preferred inorganic supports are: availability; cost; stability; ease of functionalization; particle size; surface area; pore diameter; and, pore volume. Suitable grades of aluminas, carbons, clays, glasses, silicas, and zeolites can be found which provide acceptable performance by many of these criteria. However, matrices composed of aluminum oxides (aluminas), silicon oxides (silicas) and chemical mixtures thereof, are most preferred because of their thermal and chemical stability, and the ease with which they can be functionalized. In addition, aluminas and, especially, silicas with desirable physical characteristics (particle size, surface area, pore diameter, and pore volume) are easily obtained.

The macroscopic form of the substrates that can be employed in the preparation of compositions of this invention can be varied significantly. The substrate can be in the form of beads or powder or other relatively small particles. However, using catalysts which are covalently bound to an insoluble inorganic matrix in the form of small beads is generally preferred since this simplifies removal of the bound catalyst through filtration and similar such techniques. Useful particle sizes are from 0.01 to 6 mm.

It is generally desirable that the particles of these inorganic matrices have relatively large surface areas available for functionalization. In part, this area is dependant on the average specific pore volume of the substrate particles and therefore it, also, should be relatively large. Useful surface areas are from 5 to 600 $m_2$/gram with pore volumes from 0.5 to 1.2 $cm^3_{/gram}$.

The average pore diameter of these inorganic substrates must be at least large enough to facilitate intimate contact between the reaction starting materials and the active sites on the inorganic substrate and then allow the resulting product to migrate away from the catalytic site, making the site available for further reaction. Therefore, generally, larger pore diameters are preferred. However, in those instances where the starting materials have two or more reactive sites in each molecule, it is possible, by using matrices with relatively smaller pore diameters, to limit the formation of higher molecular weight oligomers. Useful pore diameters are from 5 to 500 nm (50 to 5000 Angstroms).

The catalytically active 4-dialkylamino and 4-(N-arylalkyl-N-alkyl)amino pyridine sites may be bound to the inorganic support using a number of different approaches. The most accessible reactive species on the surface of silica and alumina particles are hydroxyl groups. These can be activated by a number of reagents. For example, they can be treated with hydrochloric or hydrobromic acid to prepare the corresponding surface bearing silicon halide or aluminum halide groups. These, in turn, can be displaced by a number of functional groups, for example, alcohols or alkoxide salts. If these reagents bear the desired catalytic sites or can be further derivatized to bear such sites, bound catalyst compositions of the current invention, can be prepared.

However, routes based upon the facile reaction of alkoxysilanes with Al—OH and Si—OH groups, losing alcohol and giving the corresponding Al—O—Si or Si—O—Si bonds, are more conveniently practiced. Silica bearing haloalkyl groups can be easily prepared by treatment of activated silica with, for example, commercially available trialkoxy 3-chloropropyl or 2-(4'(3')-chloromethylphenyl)-ethyl silane to give silica bound alkyl or arylalkyl halides. These, in turn, can be converted to catalytically active sites by reaction with, for example, an alkali metal salt of 4-methylaminopyridine. Thus prepared would be bound catalysts containing 4-(N-methyl-N-propyl)-aminopyridine groups or 4-(N-ethylbenzyl-N-methyl)aminopyridine groups, respectively.

Alternatively, it is usually preferable to follow a route where the condensation of the alkoxysilane with the alumina or silica substrate is the last step in the preparation of the bound catalyst. The required alkoxysilanes bearing catalytically active sites can be prepared by the reaction of, for example, trialkoxy 3-chloropropyl or 2-(4'(3')-chloromethylphenyl)ethyl silane with, for example, an alkali metal salt of 4-methylaminopyridine. Further, it is usually more preferable to follow a route wherein the alkoxysilyl group is added to a precursor bearing catalytically active sites as the next to last step in the synthesis sequence. This is conveniently accomplished by a noble metal catalyzed condensation of an alkoxyhydrosilane with an alkene.

Thus, the preferred routes to the compositions of this invention involve, first, the preparation of alkenes bearing catalytically active sites, for example, by the reaction of 3-chloropropene or 4(3)-chloromethylstyrene with, for example, an alkali metal salt of 4-methylaminopyridine to give 4-(N-methyl-N-3'-propenyl)aminopyridine or 4-(N-4'(3')-vinylbenzyl-N-methyl)amino-pyridine, respectively. Alkoxyhydrosilanes that are useful in the next step have the structure $HSiR3_x(OR4)_{3-x}$ (II), where $R_3$ and $R_4$ are lower alkyl, preferably, $C_1$ to $C_3$. The value of x can be 2 but it is more preferable that x be 0 or 1 so as to provide at least two points of attachment of the catalytic group to the substrate and thereby reduce the possibility that the 4-dialkylamino and 4-(N-arylalkyl-N-alkyl)amino pyridine sites will be cleaved from the substrate during subsequent processing. For example, 4-(N-methyl-N-3'-propenyl)aminopyridine or 4-(N-4'(3')-vinylbenzyl- N-methyl)aminopyridine can be treated with, for example, triethoxyhydrosilane (structure II where x is 0 and $R_4$ is $C_2H_5$) in the presence of, for example, chloroplatinic acid to give 4-(N-3'-triethoxylsilyl-propyl-N-methyl)-aminopyridine or 4-N-(4'(3')-(2-triethoxysilylethyl)benzyl)-N-methyl)aminopyridine, respectively. The final step, the reaction of alkoxysilanes bearing catalytically active sites with the inorganic substrate, is, preferably, carried out by simply mixing the reagents and an inert solvent, whose boiling point is somewhat higher than the expected byproduct alcohol, and removing the byproduct alcohol by slowly distilling off a portion of the solvent. For example, when the preferred methoxy, ethoxy or propoxy silanes are used, toluene is an especially convenient solvent for this reaction.

By controlling the amount of alkoxysilane used, it is also possible to adjust the number of catalytically active sites bound to the inorganic matrix. From a practical standpoint, the minimum required number of active sites on the catalyst is that amount that provides a "catalytically effective amount", i.e., an amount sufficient to catalyze the desired reaction. The upper limit is, in one sense, defined by the composition of the catalyst and the substrate to which it is being bound. This maximum is, in practice, determined by the amount that provides a catalyst that permits some control over the desired reaction. Additionally, the active site content of the bound catalyst which provides a practically useful catalyst is also a function of the activity of the catalyst that is bound to the substrate. Generally, it is found that for the types of reactions for which the catalytic compositions of this invention are useful, the range of 0.01 to 10 meq of catalytic sites per gram of substrate is preferred, with levels of 0.1 to 5 meq per gram being most preferred.

There are at least two options with respect to the manner in which the reactant(s), optionally in the presence of a solvent, can be contacted with the catalyst compositions of this invention, either (a) packed in a cartridge or tube, or (b) dispersed in a stirred reactor. In either case, the system can be operated in batches, e.g., where the system is charged with reactant(s), the reaction is typically run until the desired extent of reaction is reached, and then the product stream is separated from the catalyst by filtration or similar such means. Alternatively, the system can be run as a continuous process wherein a starting material feed is continuously added to the system while a product stream having the desired extent of reaction is continuously withdrawn. Potential hardware configurations include: a Continuously Stirred Tank Reactor ("CSTR") with the catalyst dispersed in the reaction medium; a CSTR which serves as a reservoir for a mixture of starting material(s) and product that is repetitively passed, in parallel, through a battery of catalyst packed cartridges, wherein relatively low levels of reaction are achieved in each pass; or a catalyst packed tube, wherein the desired extent of reaction is reached in a single pass through the tube.

When using the catalyst compositions, a range of bound catalyst concentrations may be employed to achieve the desired reaction product. The factors to be considered in the selection of preferred catalyst concentrations are: the activity of the catalyst being used; the degree of conversion desired; and, the temperature at which the reaction is conducted. Generally, levels between 0.1 and 75 parts of bound catalyst per 100 parts of precursor isocyanate are preferred. Levels between 1 and 50 parts of catalyst per 100 parts of precursor isocyanate are most preferred.

The catalyst compositions of the present invention are suitably employed in the production of a wide range of isocyanate dimers, including hexamethylene diisocyanate ("HDI") dimer, isophorone diisocyanate ("IPDI") dimer, $H_{12}MDI$ dimer, toluene diisocyanate ("TDI") dimer, methylene diphenylene diisocyanate ("MDI") dimer, naphthalene diisocyanate ("NDI") dimer, cyclohexylene diisocyanate ("CHDI") dimer, 1,4-phenylene diisocyanate ("PPDI") dimer, bitolyene diisocyanate ("TODI") dimer, xylene diisocyanate ("XDI") dimer, tetramethyl xylene diisocyanate ("TMXDI") dimer, 1,3-bis(isocyanatomethyl) cyclohexane ("$H_6MDI$") dimer, and the like, as well as, mixtures thereof. In addition, other compounds are suitably prepared using the catalyst compositions of the present invention, esters, acylated ketones, allophanates (when an alcohol is employed in the reaction mixture), biurets (when water is employed in the reaction mixture), and the like.

The following examples are intended to illustrate, but in no way limit the scope of, the present invention.

EXAMPLE 1

A—Preparation of a Silica Bound 4-Bis(3'-methylsilylpropyl)-aminopyridine Catalyst 4-Diallylaminopyridine was prepared by the condensation of 4-chloropyridine with diallylamine, as described by Mathias and Cei (Macromolecules, 1987, 20, 2645). This product was hydrosilylated with diethoxymethylsilane in the presence of chloroplatinic acid, as described by Rubinsztajn, et al, (Macromolecules, 1990, 23, 4026) to yield 4-bis(3'-diethoxymethylsilylpropyl)aminopyridine. Finally, following a procedure similar to that described by Tundo and Venturello (J. Amer. Chem. Soc., 1979, 101, 6606), this product (14.1 gm, 0.032 mol) was added to a 500 ml round bottom flask, equipped with a magnetic stirrer and a distillation head, containing 250 ml of toluene and 39.8 gm activated silica (Davison Grade 22, 60–200 mesh, 60 Angstrom, 500 $m^2$/gram BET surface area, 0.75 $cm^3$/gram pore volume). The mixture was stirred and heated to distill off about 125 ml of a toluene and ethanol solution over a period of about 3 hours. The resulting silica bound dialkylaminopyridine was separated from the reaction mixture by filtration, washed with three 100 ml portions of methanol and then finally washed with 100 mls of diethyl ether. After drying in a vacuum oven at 45° C. for 18 hours, the product was found to contain 0.6 meq aminopyridine/gram.

B—Acylation of Hydroquinone

The procedure of D. Johnston, Chem. Ind., 24, 1000 (1982), for demonstrating the beneficial activity of DMAP in this reaction, was followed. A sample (1.1 gm) of the above silica bound catalyst was mixed with 200 gm ethyl acetate and 10.9 gm (0.1 mol) hydroquinone. To this suspension was added 10.2 gm (0.11 mol) triethylamine and 11.0 gm (0.11 mol) acetic anhydride. The mixture was stirred for 1.6 hours at room temperature and then filtered to remove the catalyst. Volatile components were removed, using a rotary evaporator, to give 13.5 grams of crude product. The pure hydroquinone monoacetate (9.3 gm, 55% yield), was isolated by chromatography on silica gel with chloroform/methanol (9:1, v/v). Its structure was confirmed by melting point (63° to 64° C.) and its IR and NMR spectra.

C—Preparation of 1-Methylcyclohexyl Acetate

The procedure given in a product publication, "POLYDMAP(tm) POLYMER, A Guide to Its Successful Use", Reilly Industries, 1990, for testing the activity of polystyrene bound BMAP, was followed. A sample (7.0 gm) of the above silica bound catalyst was mixed with 8.2 gm (0.07 mol) 1-methylcyclohexanol. To this suspension was added 11.6 gm (0.12 mol) triethylamine and 12.8 gm (0.13 mol) acetic anhydride. The mixture was heated at reflux for 5 hours, then filtered to remove the catalyst. The catalyst was washed with 50 ml dichloromethane. The combined filtrate and washes were treated with three 50 ml portions of 9% aqueous HCl, then with three 50 ml portions of saturated aqueous sodium bicarbonate. The organic layer was then dried over anhydrous magnesium sulfate, filtered and the volatile components were removed using a rotary evaporator. The crude product was purified by vacuum distillation through a short Vigreux column. Analysis of the distilled fractions by vapor phase chromatography showed that the desired 1-methylcyclohexyl acetate was obtained in 90% yield.

The recovered catalyst was cycled through this same procedure three times without any apparent lose in activity.

D—HDI Dimerization Test

To 10 gm of the above silica bound catalyst was added 100 gm HDI. The mixture was stirred and heated at 60° to 70° C. for 6 hours. An IR spectrum of the liquid showed that at least 15% of the HDI had been converted to dimer. No absorptions due to isocyanurates were detected.

E—TDI Dimerization Test

To 1.0 gm of the above silica bound catalyst was added 15 gm TDI (composed 80% 2,4-TDI and 20% 2,6-TDI). The mixture was stirred and heated at 65° C. for 15 minutes. An IR spectrum of the liquid showed that least 10% of the TDI had been converted to dimer. No absorptions due to isocyanurates were detected.

F—IPDI Dimerization Test

To 1.0 gm of the above silica bound catalyst was added 15 gm IPDI. The mixture was stirred and heated at 60° to 62° C. for 6 hours. An IR spectrum of the liquid showed that at least 20% of the IPDI had been converted to dimer. No absorptions due to isocyanurates were detected.

EXAMPLE 2

A—Dimerization Test—Stopping the Reaction

To 30 gm of the silica bound catalyst, prepared in Example 1A, was added 134.4 gm HDI. The mixture was stirred and heated to 70° to 75° C. for approximately 4 hours. At this point an IR spectrum of the liquid showed that 18% of the HDI had been converted to dimer. The mixture was filtered under nitrogen through a sintered glass filter funnel. About 100 ml of the filtrate was then heated to 70° to 75° C. for 4 hr. During the heating period and at the end the IR spectra showed no increase or decrease in dimer concentration (18%).

B—Dimerization Test—Continuing the Reaction

To 30 gm of the silica bound catalyst, prepared in Example 1A, was added 117.3 gm HDI. The mixture was stirred and heated to 70° to 75° C. for approximately 4 hours. At this point an IR spectrum of the liquid showed that 22% of the HDI had been converted to dimer. Most of the supernatant liquid (97.6 gm) was decanted from the catalyst and 102.7 gm fresh HDI was added. This mixture was heated at 70° to 75° C. for 4 hours. An IR spectrum of the liquid showed that 24% of the HDI had been converted to dimer. This process of decanting the supernatant liquid, adding fresh HDI and then heating was repeated an additional two times with no apparent loss in activity of the catalyst.

EXAMPLE 3

Preparation of HDI Dimer

To a 1 L flask equipped with a mechanical stirrer, thermometer, nitrogen inlet and a condenser was added 500 gms of HDI and 100 gms of the silica bound catalyst prepared in Example 1A. The mixture was heated and stirred at 80° C. for 6 hours. An IR spectrum of the liquid showed that 25% of the HDI had been converted to dimer. Most of the supernatant liquid (406 gms) was siphoned from the catalyst using a filter stick and 450 gms of fresh HDI were added. The mixture was heated and stirred at 80° C. for 6 hours. An IR spectrum of the liquid showed that 23% of the HDI had been converted to dimer. This process of removing the supernatant liquid, adding fresh HDI and then heating was repeated an additional four times with no apparent loss in activity of the catalyst.

The product fractions were combined and stripped of residual monomer using a wiped film evaporator. The resulting product weighed 614.5 grams, had a color value of 55 APHA and its IR spectrum showed no absorptions due to isocyanurates. The viscosity of the product was 60 cps at 25° C.

EXAMPLE 4

A—Preparation of an Alumina Bound 4-Bis(3'-methylsilylpropyl)-aminopyridine Catalyst Following a procedure similar to that described by Tundo, et al, (J. Amer. Chem. Soc., 1982, 104, 6547) and in Example 1A, 4-bis(3'-diethoxymethylsilylpropyl) aminopyridine, as prepared in Example 1A, was heated with activated alumina (Aldrich 26,774-0, 150 mesh, 58 Angstrom, 155 $m^2$/gram BET surface area), to give the alumina bound dialkylaminopyridine. After drying in a vacuum oven at 45° C. for 18 hours, this material was found to contain 0.2 meq aminopyridine/gram.

B—Dimerization Test

To 40 gm of the above alumina bound catalyst was added 100 gm HDI. The mixture was stirred and heated at 70° to 80° C. for 6 hours. An IR spectrum of the liquid showed that at least 15% of the HDI had been converted to dimer. No absorptions due to isocyanurates were detected.

EXAMPLE 5

A—Preparation of a Silica Bound 4-N(4'(3')-(2-silylethyl)benzyl)-N-methylaminopyridine Catalyst 4-N-(4'(3')-vinylbenzyl)-N-methylaminopyridine was prepared by the condensation of 4(3)-vinylbenzylchloride with the sodium salt of 4-methylaminopyridine, as described by Tomoi, et al, (Macromol. Chem. Rapid Commun., 1982, 3, 537). This product was hydrosilylated with triethoxysilane in the presence of chloroplatinic acid and BHT, in a procedure similar to that described by Rubinsztajn, et al, (Macromolecules, 1990, 23, 4026) to yield 4-N-(4'(3')-(2-triethoxy-silylethyl) benzyl)-N-methylaminopyridine. Finally, following a procedure similar to that described by Tundo and Venturello (J. Amer. Chem. Soc., 1979, 101, 6606) and in Example 1A, this product was heated with activated silica (Davison Grade 22, 60–200 mesh, 60 Angstrom, 500 $m^2$/gram BET surface area, 0.75 $cm^3$/gram pore volume), to give the silica bound arylalkyl-alkyl-aminopyridine with the loss of ethanol. After drying in a vacuum oven at 45° C. for 18 hours, this material found to contain 0.4 meq aminopyridine/gram.

B—Dimerization Test

To 35 gm of the above silica bound catalyst was added 100 gm HDI. The mixture was stirred and heated at 70° to 80° C. for 6 hours. An IR spectrum of the liquid showed that at least 20% of the HDI had been converted to dimer. No absorptions due to isocyanurates were detected.

While the compositions of this invention have been described above with references to specific embodiments thereof, it is apparent that many changes, modifications and variations in the materials, arrangements of parts and steps can be made without departing from the inventive concept disclosed herein. Accordingly, the spirit and broad scope of the appended claims is intended to embrace all such changes, modifications and variations that may occur to one of skill in the art upon a reading of the disclosure. All patent applications, patents and other publications cited herein are incorporated by reference in their entirety.

What is claimed is:

1. A catalyst composition having the following empirical structural formula:

cat-(—Si—(—O-inorg substr)$_m$)$_n$ wherein "cat" denotes an aminopyridine catalyst selected from the group consisting of 4-dialkylamino and 4-(N-arylalkyl-N-alkyl)-aminopyridines, and combinations thereof, wherein "inorg substr" denotes an inorganic substrate selected from the group consisting of silica compounds, alumina compounds, and combinations thereof, wherein m is between one and three, and wherein n is between one and two, said aminopyridine catalyst having the structure Pyr-NR1R2 wherein Pyr is a 4-pyridinyl residue, and $R_1$ and $R_2$ are, independently from one another, $C_1$ to $C_6$ alkyl or $C_7$ to $C_{12}$ arylalkyl groups, or, $R_1$ and $R_2$, taken together with the attached nitrogen, form a ring optionally containing another heteroatom selected from the group consisting of oxygen, nitrogen, sulfur, and combinations thereof.

2. The catalyst composition of claim 1 wherein said catalyst additionally contains nitrogen- containing or phosphorus-containing functional groups, or a combination thereof.

3. The catalyst composition of claim 1 wherein said catalyst contains catalytic sites in an amount of between about 0.01 and about 10 milliequivalents of catalytic sites per gram of inorganic substrate.

4. The catalyst composition of claim 1 wherein said inorganic substrate is selected from the group consisting of aluminas, carbons, clays, glasses, silicas, zeolites, and combinations thereof.

5. A catalyst composition comprising the reaction product of:

(A) an inorganic substrate containing a reactive hydroxyl group and selected from the group consisting of silica compounds, alumina compounds, and combinations thereof, (B) an aminopyridine catalyst containing terminal unsaturation and selected from the group consisting of 4-dialkylamino and 4-(N-arylalkyl-N-alkyl)-aminopyridines, and combinations thereof, said aminopyridine catalyst having the structure Pyr-NR1R2 wherein Pyr is a 4-pyridinyl residue, and $R_1$ and $R_2$ are, independently from one another, $C_1$ to $C_6$ alkyl or $C_7$ to $C_{12}$ arylalkyl groups, or, $R_1$ and R2, taken together with the attached nitrogen, form a ring optionally containing another heteroatom selected from the group consisting of oxygen, nitrogen, sulfur, and combinations thereof, and (C) a hydrosilane.

6. The catalyst composition of claim 5 wherein said catalyst additionally contains nitrogen-containing or phosphorus-containing functional groups, or a combination thereof.

7. The catalyst composition of claim 5 wherein said catalyst contains catalytic sites in an amount of between about 0.01 and about 10 milliequivalents of catalytic sites per gram of inorganic substrate.

8. The catalyst composition of claim 5 wherein said inorganic substrate is selected from the group consisting of aluminas, carbons, clays, glasses, silicas, zeolites, and combinations thereof.

9. A process for preparing a catalyst composition which comprises the steps of:

(a) reacting a terminally unsaturated aminopyridine catalyst selected from the group consisting of 4-dialkylamino and 4-(N-arylalkyl-N-alkyl)-aminopyridines, and combinations thereof, said aminopyridine catalyst having the structure Pyr-NR1R2 wherein Pyr is a 4-pyridinyl residue, and $R_1$ and $R_2$ are, independently from one another, $C_1$ to $C_6$ alkyl or $C_7$ to $C_{12}$ arylalkyl groups, or, $R_1$ and $R_2$, taken together with the attached nitrogen, form a ring optionally containing another heteroatom selected from the group consisting of oxygen, nitrogen, sulfur, and combinations thereof, with a hydrosilane to cause hydrosilanization of the catalyst, thereby providing a hydrosilanized catalyst containing at least one -SiX moiety wherein "X" is halogen or OR wherein "R" is an alkyl group of 1–25 carbons, and (b) reacting said hydrosilanized catalyst with an inorganic substrate containing a reactive hydroxyl group and selected from the group consisting of silica compounds, alumina compounds, and combinations thereof, to provide an inorganic substrate-bound catalyst composition characterized by the presence of at least one siloxy linking moiety providing covalent bonding between said catalyst and said substrate.

10. The process of claim 9 wherein said catalyst additionally contains nitrogen- containing or phosphorus-containing functional groups, or a combination thereof.

11. The process of claim 9 wherein said catalyst contains catalytic sites in an amount of between about 0.01 and about 10 milliequivalents of catalytic sites per gram of inorganic substrate.

12. The process of claim 9 wherein said inorganic substrate is selected from the group consisting of aluminas, carbons, clays, glasses, silicas, zeolites, and combinations thereof.

13. The process of claim 9 wherein said inorganic substrate is an insoluble matrix, wherein said catalyst has between 0.1 and 10 miliequivalents of catalytic sites per gram of said insoluble matrix, and wherein said insoluble matrix has a pore diameter of between 5 and 500 nanometer, and a surface area of between 5 and 600 square meters per gram and a pore volume of between 0.5 and 1.2 cubic centimeters per gram of said insoluble matrix.

14. The catalyst composition of claim 1 wherein said inorganic substrate is an insoluble matrix, wherein said catalyst has between 0.1 and 10 miliequivalents of catalytic sites per gram of said insoluble matrix, and wherein said insoluble matrix has a pore diameter of between 5 and 500 nanometer, and a surface area of between 5 and 600 square meters per gram and a pore volume of between 0.5 and 1.2 cubic centimeters per gram of said insoluble matrix.

15. The catalyst composition of claim 5 wherein said inorganic substrate is an insoluble matrix, wherein said catalyst has between 0.1 and 10 miliequivalents of catalytic sites per gram of said insoluble matrix, and wherein said insoluble matrix has a pore diameter of between 5 and 500 nanometer, and a surface area of between 5 and 600 square meters per gram and a pore volume of between 0.5 and 1.2 cubic centimeters per gram of said insoluble matrix.

* * * * *